(12) United States Patent
Achar

(10) Patent No.: US 9,529,741 B2
(45) Date of Patent: Dec. 27, 2016

(54) CONFIGURABLE MULTIPORT MEDICAL INTERFACE DEVICE

(71) Applicant: General Electric Company, Schenectady, NY (US)

(72) Inventor: Nagesh Mysore Lakshminarayan Achar, Bangalore (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/674,311

(22) Filed: Mar. 31, 2015

(65) Prior Publication Data

US 2016/0292089 A1     Oct. 6, 2016

(51) Int. Cl.
*G06F 3/00* (2006.01)
*G06F 13/00* (2006.01)
*G06F 13/14* (2006.01)
*G06F 13/10* (2006.01)
*G06F 9/445* (2006.01)
*G06F 19/00* (2011.01)

(52) U.S. Cl.
CPC ......... *G06F 13/102* (2013.01); *G06F 9/44505* (2013.01); *G06F 19/3406* (2013.01)

(58) Field of Classification Search
None
See application file for complete search history.

(56) References Cited

U.S. PATENT DOCUMENTS

| 8,621,489 | B2 | 12/2013 | McQuaid et al. | |
| 9,008,658 | B2 * | 4/2015 | Baker | G06F 19/3418 340/539.12 |
| 2008/0147442 | A1 * | 6/2008 | Warner | A61G 7/018 705/3 |
| 2013/0006666 | A1 * | 1/2013 | Schneider | G06F 19/322 705/3 |
| 2013/0109929 | A1 * | 5/2013 | Menzel | G06F 19/3406 600/301 |
| 2013/0297350 | A1 * | 11/2013 | Gross | G06F 19/327 705/3 |
| 2013/0317753 | A1 * | 11/2013 | Kamen | G06F 19/3412 702/19 |
| 2015/0190208 | A1 * | 7/2015 | Silveira | A61B 5/14551 600/301 |

* cited by examiner

*Primary Examiner* — David E Martinez
(74) *Attorney, Agent, or Firm* — Boyle Fredrickson, S.C.

(57) ABSTRACT

A multiport interface device and method of use in a patient data routing system for connecting peripheral devices to one or more patient monitors is provided. The multiport interface device is configurable to directly route data signals received in one or more of the input ports of the interface device to one or more specified output ports of the interface device. The routing of the data can be accomplished by port slicing of the interface device and/or by utilizing coded adapters engaged at the input and output ports of the interface to route signals from multiple peripheral devices to a patient monitor, as necessary.

13 Claims, 2 Drawing Sheets

CONFIGURABLE MULTIPORT MEDICAL INTERFACE DEVICE

BACKGROUND OF THE INVENTION

The invention relates generally to interface devices for connecting peripheral medical devices to patient monitors for transmitting data about a patient from the peripheral device to the monitor via the interface, and more particularly to a device and method for providing simultaneous data from peripheral medical devices to multiple patient monitors for bedside device data aggregation.

In current practice, various interface devices, such as UnityID, Vuelink, IDM-MG3000 and similar devices, are utilized to connected peripheral patient devices with patient monitors to enable patient data obtained by the peripheral devices to be displayed on the monitors. These interface devices are configured as multiport interface devices which can simultaneously receive physiological data from peripheral devices that are connected directly to a patient, such as ventilators, IV pumps, CCO devices, and the like, and provide and/or direct the data either to the patient monitor or to the respective monitoring network connected to the interface device. With these types of interface devices, up to eight peripheral devices can be connected to a single interface device for simultaneously receiving data from the peripheral devices and forwarding the data to a single patient monitor also connected to the interface device. To accomplish this, these multiport interface devices contain customized drivers for the proper operation of the interface device in forwarding the data received from the peripheral devices to the connected patient monitor in order to avoid data mixing within the interface device.

In many of the care areas in a hospital where these interface devices are utilized, less than eight (8) peripheral devices will be used for a single patient, because many patient monitors include certain parameter module(s) within the monitor itself. As a result, often, only 2-3 ports of the interface device are utilized for a patient, with 5-6 ports of the interface device being vacant or not used.

From the standpoint of a customer or end user of these interface devices, this presents an issue, i.e., connecting a single patient to a single interface device for data integration, as a large number of multiple port interface devices need to be purchased by the customer to enable the connection of the multiple peripheral devices for each patient to the interface device and associated patient monitor. These multiple port devices for a single purpose/patient become an asset to the hospital, and these assets needs to be tracked and maintained.

In addition, when using these multiport interface devices, the vacant ports on the multiport interface device can often be connected to peripheral devices that provide data coming from a different patient. In these situations, the clinical information systems recording the data received by and forwarded from the multiport interface device can potentially have mixed patient data from different patients that is recorded as a single patient record, thus creating a number of safety and treatment related issues.

From the perspective of the interface device manufacturer, all of the devices that are manufactured, e.g., single port, dual port, and multiport devices have to be maintained and able to be utilized with the various peripheral devices that can be connected to the interface device, many of which have different and unique operating drivers. The consequent development cost and maintenance costs to provide interface devices to accommodate this situation are high for these interface devices as a result.

One example of an interface device that attempts to address this issue is disclosed in U.S. Pat. No. 8,621,489, incorporated herein by reference in its entirety. In the '489 patent, the interface device includes a device supervisor component that is capable of reconfiguring the framework components of the interface device in order to accommodate/enable the interface device to communicate with the particular driver(s) for the peripheral devices connected to the interface device. This is accomplished by the supervisor component generating a reusable plug-and-play extensible markup language driver file that can be selected by the user when a peripheral device employing that driver and which is used by the supervisor component to configure the interface device to accommodate the driver for the particular peripheral device.

However, in utilizing an interface device of this type, the complexity of the interface device required to include the supervisor component and the associated driver files renders the interface device difficult to implement in many situations. Further, the interface device in the '489 patent does not address the issue of peripheral devices from multiple patients being improperly connected to the same interface device, and the consequent data mixing issues.

As a result, an improved multiport interface device is needed to enable the device to be utilized more efficiently while also reduce the potential or likelihood serious errors that can cause mixing of patient data records when connecting multiple peripheral devices to the multiport interface device.

BRIEF DESCRIPTION OF THE INVENTION

According to one aspect of an exemplary embodiment of the invention, a multiport interface device and method of use in a patient data routing system for connecting peripheral devices to one or more patient monitors is provided. The multiport interface device is configurable to directly route data signals received in one or more of the input ports of the interface device to one or more specified output ports of the interface device via port slicing. Thus, depending upon the situation in which the multiport interface device is to be utilized, the interface device can be configured to route signals from multiple peripheral devices connected to the input ports of the interface device to a single or multiple patient monitors operably connected to the output ports on the interface device. The interface device can additionally be configured to route signals from multiple peripheral devices to multiple patient monitors, as necessary.

According to another aspect of an exemplary embodiment, the interface device can be utilized with one or more patient identification and communication adapters (PIDCA). The adapters include a communication component, for receiving patient identification information, and a storage component, in which the patient identification information can be stored. Once the patient identification information is received and stored on the PIDCA, the PIDCA can be engaged with an input port of the interface device, such that a connection between a peripheral device and the input port of the interface device is made through the PIDCA. The PIDCA can "tag" data received by the interface device from the peripheral device with the patient identification information, such that the data is able to be routed by the interface device to an output port engaged with another PIDCA having a matching "tag", i.e., on which matching patient information is stored. In using the PIDCAs, should any of the peripheral devices be connected to input ports on the interface device not configured to direct the incoming data to the correct output port/patient monitor, the presence of the PIDCA effectively re-routes the data to the appropriate patient monitor, avoiding any data mixing issues.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings.

DETAILED DESCRIPTION OF THE DRAWINGS

In the present description, certain terms have been used for brevity, clarity and understanding. No unnecessary limitations are to be implied therefrom beyond the requirement of the prior art because such terms are used for descriptive purposes only and are intended to be broadly construed. The different systems and methods described herein may be used alone or in combination with other systems and methods. Various equivalents, alternatives, and modifications are possible within the scope of the appended claims. Each limitation in the appended claims is intended to evoke interpretation under 35 USC §112, sixth paragraph, only if the terms "means for" or "step for" are explicitly recited in the respective limitation.

Figure 1:
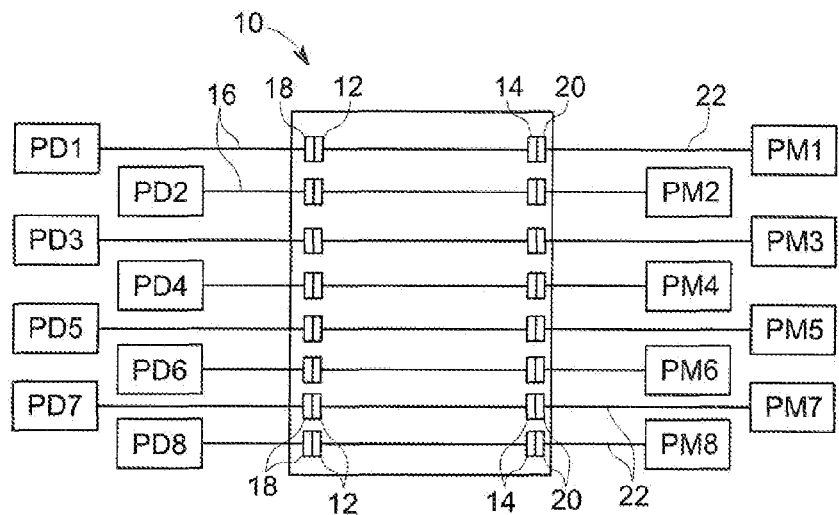
FIG. 1 is a schematic view of an interface device according to one embodiment of the present invention.

Referring to FIG. 1, in an exemplary embodiment of the invention, a patient data system employs a multiport interface device illustrated at 10 that includes a number of input ports 12 and output ports 14. The input ports 12 are configured to be operably connected to cables 16 extending from various peripheral devices PD1-PD8, which can include, but are not limited to, ventilators, anesthesia devices, and intravenous pumps, among others. The cables 16 include suitable connectors 18 that can be engaged with complementary structures on the inlet ports 12. In this manner, data obtained by the peripheral devices PD1-PD8 from a patient to which the devices PD1-PD8 are connected can be transmitted from the devices PD1-PD8 to the interface device 10 via the cables 16. The connectors 18 can have any suitable configuration that is connectable to the input port 14, as is known in the art. Further, the input ports 12 may be formed with a single complementary structure for receiving the connector 18, or can be formed with multiple complementary structures to enable the input port 12 to be connected to connectors 18 of different types.

The output ports 14 are configured similarly to the input ports 12, and are engaged by connectors 20 located on cables 22 extending from patient monitors PM1-PM8, which can be any suitable type of patient monitor, as is known in the art. In this manner, data received by the interface device 10 from the peripheral devices PD1-PD8 can be routed from the interface device 10 to patient monitors PM1-PM8 via the cables 22.

In the illustrated exemplary embodiment, the interface device 10 is configured to have the same number of input ports 12 and output ports 14 that can feed data from the peripheral devices PD1-PD8 through the interface device 10 to the patient monitors PM1-PM8. However, the interface device 10 can additionally be configured to have different numbers of input ports 12 and output ports 14, as desired To direct the data from the peripheral devices PD1-PD8 to the associated patient monitors PM1-PM8, the multiport interface device 10 is port-sliced according to the needs of the particular care environment in which the device 10 is employed, in order to associate the various input ports 12 with one or more of the output ports 14 on the interface device 10. In other words, the end user of the interface device 10 can selectively configure the multiport interface device 10 according to the particular requirements of the end user or the care area in which the device 10 is to be employed. This is accomplished in any suitable manner, such as by the end user configuring the interface device through the use of software in the device 10 or by utilizing an intelligence system (not shown) present within the interface device 10 that can operate to detect how many unique patient identification and communication adapter (PIDCA) (see FIGS. 4-6) are connected to the interface device 10, thereby port-slicing the interface device 10.

Figure 2:
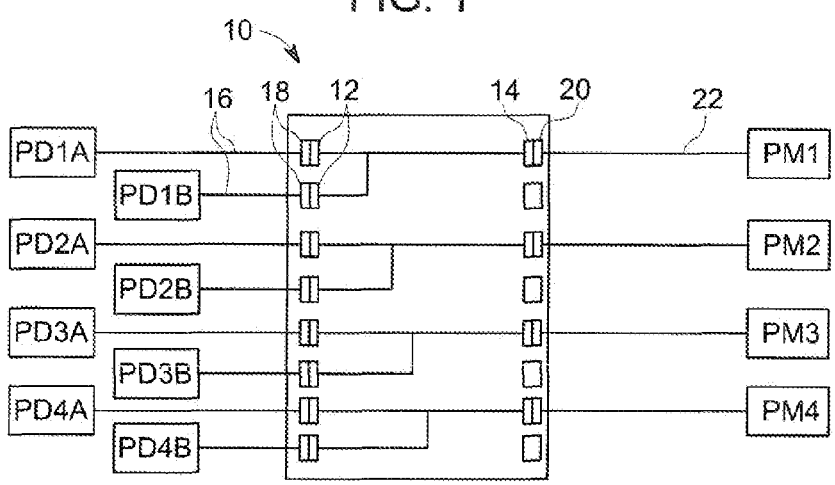
FIG. 2 is a schematic view of an interface device according to another embodiment of the present invention.
Figure 3:
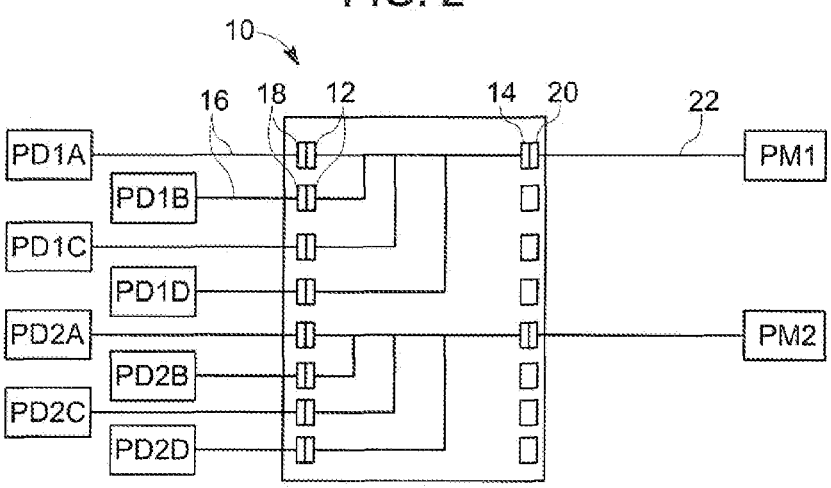
FIG. 3 is a schematic view of an interface device according to another embodiment of the present invention.

As a result of the ability of the interface device 10 to be configured in this manner, a single interface device 10 can be utilized in different manners, such as, for example, the exemplary embodiments shown in FIGS. 1-3:

1. Eight (8) independent peripheral devices PD1-PD8 connected via the interface device 10 to eight (8) separate patient monitors PM1-PM8 (FIG. 1)
2. Four (4) pairs of peripheral devices PD1A and 1B-PD4A and 4B each connected via the interface device 10 to four (4) separate patient monitors PM1-PM4 (FIG. 2)
3. Two (2) sets of four (4) peripheral devices PD1A-D and PD2A-D each connected via the interface device 10 to two (2) patient monitors PM1 and PM2 (FIG. 3)

In a situation where only one peripheral device needs to be connected to the interface device 10 for each patient, the interface device 10 can be configured as an 8-bed interface device 10, as shown in the exemplary embodiment illustrated in FIG. 1. One advantage of the 8-bed configured interface device 10 is that eight different peripheral devices PD1-PD8 from 8 different patients can be connected to the interface device 10 via the input ports 12 and the individual data from each peripheral device PD1-PD8 can be routed through the interface device 10 to eight different patient monitors PM1-PM8 for bedside integration with each monitor PM1-PM8. In particular, in an ICU care area where the beds are situated in one care area, instead of using eight (8)

separate interface devices 10, this configuration for the interface device 10 requires only one interface device 10 to serve all eight (8) patients.

Looking now at the exemplary embodiment of FIG. 2, in another situation where pairs of peripheral devices PD1A-1B to PD4A-4B need to be interfaced simultaneously to one or more patients, the multiport interface device 10 can be configured as a 4-bed interface device 10. In this embodiment, while all of the input ports 12 are connected to a peripheral device PD1A-1B to PD4A-4B, only four (4) of the output ports 14 are being utilized by patient monitors PM1-PM4. As such, the interface device 10 enables a pair of different peripheral devices (PD1A-1B) for the same patient to be connected with the interface device 10 with the data from the pair of peripheral devices PD1A-PD1B routed via the interface device 10 to a single patient monitor PM1-PM4 connected to one of the output ports 14.

Looking now at the exemplary embodiment of FIG. 3, in still another situation where sets of four (4) peripheral devices (PD1A-PD1D) need to be interfaced simultaneously for a single patient, the multiport interface device 10 can be configured as a 2-bed interface device. In this exemplary embodiment, similarly to the embodiment of FIG. 2, while all of the input ports 12 are connected to a peripheral device PD1A-1D or PD2A-2D, only two (2) of the output ports 14 are being utilized by patient monitors PM1 and PM2. As such, the interface device 10 enables four different peripheral devices (PD1A-1D) connected to the same patient to be connected with the interface device 10, with the corresponding patient data from each set of four (4) peripheral devices PD1A-PD1D and PD2A-PD2D routed via the interface device 10 to a single patient monitor PM1 or PM2 connected to one of the output ports 14.

In each of these configurations for the interface device, one significant challenge is to ensure the particular PD connected to the open input ports on the interface device sends data to the appropriate PM channel/output port, so that patient data is not mixed up due to user error. This can be accomplished by making patient identification interface cables, as illustrated in the exemplary embodiments of FIGS. 4-6.

Looking at the exemplary embodiment of FIG. 2, in situations where two peripheral devices need to be interfaced simultaneously to one or more patients, the multiport interface device can be configured as a 4-bed interface device. The advantage of the configured 4-bed interface device is that two different peripheral devices (PD1) for the same patient can be interfaced and the data transferred to the single patient monitor (PM1) connected to one of the output ports. For instance two PD1 data can reach simultaneously to PM1, two PD2 to PM2, two PD3 to PM3 and two PD4 to PM4.

Looking now at the exemplary embodiment of FIG. 3, in situations where four peripheral devices need to be interfaced simultaneously for a single patient, the multiport bridge can be configured as a 2-bed interface device. The advantage of the configured 2-bed interface device is that four different peripheral devices (PD1) for the same patient can be interfaced and the data transferred to the single patient monitor (PM1) connected to a single output port on the interface device. For instance four PD1 data can reach simultaneously to PM1 and four PD2 to PM2.

In each of these exemplary configurations for the interface device 10, it is also necessary to ensure that the particular peripheral device PD1-PD8 connected to one of the input ports 12 on the interface device 10 sends data through the interface device 10 to the appropriate output port 14 and associated patient monitor PM1-PM8 so that patient data is not mixed. In one exemplary embodiment, this can be accomplished by suitable labeling of the input ports 12, such as by color-coding the input ports 12 and output ports 14. This can also be accomplished by labeling the cables 16 and 22, either by color-coding the cables or in another suitable manner.

Figure 4:
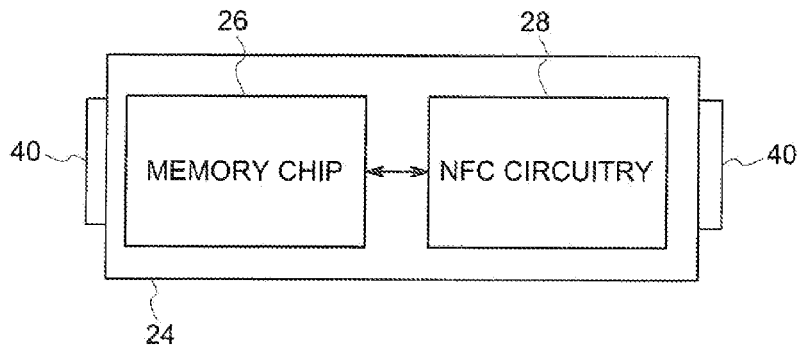
FIG. 4 is a schematic view of a patient identification and communication adapter (PIDCA) for use with an interface device according to one embodiment of the present invention.
Figure 5:
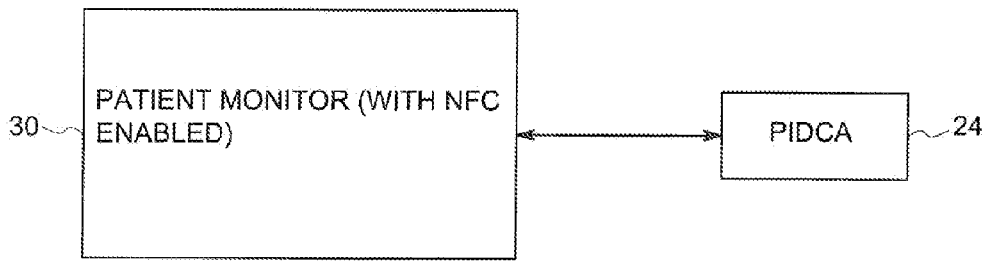
FIG. 5 is a schematic view of the communication of the PIDCA with a patient monitor according to one embodiment of the present invention.
Figure 6:
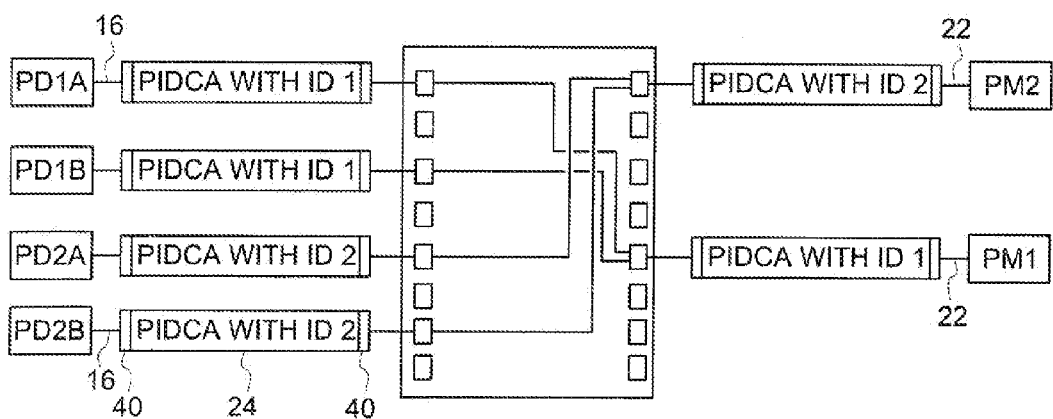
FIG. 6 is a schematic view of a number of PIDCAs utilized with an interface device according to one embodiment of the present invention.

In one other exemplary embodiment, as illustrated in FIGS. 4-6, the cables 16 and 22 can also be labeled to avoid the mixing of patient data for clinical use by employing a patient identification and communication adapter (PIDCA) device 24. The PIDCA 24, as shown in an exemplary schematic embodiment in FIG. 4, includes a pair of connectors 40 that enable the PIDCA 24 to be operably connected to the connector 18,20 of an associated cable 16,22 and to either an input port 12 or an output port 14 of the interface device 10, such that the PIDCA 24 interconnect the cables 16,22 with the interface device 10 to enable data to ben sent along the cables 16,22 to and from the interface device 10.

The internal components of the PIDCA 24 can include a small memory unit or chip 26 or other suitable and optionally re-writeable memory unit that is operably connected to the connectors 40 and operates to receive, store transmit identification information and/or the admissions, discharge and transfer (ADT) information for a particular patient. The PIDCA 24 also includes a near-field communication (NFC) component 28 operably connected to the memory chip 26. The NFC 28 is constructed to wirelessly operate to communicate with a patient monitor (PM) 30 or other suitable device that is NFC-enabled to enable the NFC 28 to obtain the patient identification information from the PM 30. In one exemplary embodiment, the PIDCA 24 can obtain the required patient ID information by touching or placing the PIDCA 24 in close proximity to the PM 30 in order for the PM 30 to wirelessly transmit the patient information to the PIDCA 24. In an alternative embodiment, the PIDCA 24 can be connected to the PM 30 or other suitable device to receive the patient ID information, as well as potentially to charge a battery (not shown) disposed within the PIDCA 24 and operably connected to the chip 26 and NFC 28 to power them.

More specifically, in the exemplary embodiment of FIG. 5, when the PIDCA 24 is brought near to the NFC-enabled patient monitor 30, the patient ID information that is already present and stored in the PM 30 is wirelessly communicated to the NFC 28 in the PIDCA 24, and subsequently stored by the PIDCA 24 in the memory chip 26. In this manner, the PIDCA 24 is encoded with the patient ID information.

Referring now to the exemplary embodiment of the invention shown in FIG. 6, one PIDCA 24 on which patient ID 1 is stored is attached via one connector 40 to the connector 18 on the cable 16 extending from the patient peripheral device (PD1A) connected to the patient associated with the patient ID 1 that stored in the memory unit/chip 26 of the PIDCA 24. The other connector 40 on the PIDCA 24 can then be used to operably connect the cable 16 to an input port 12 of the multiport interface device 10.

Similarly, a separate PIDCA 24 having the same stored patient ID 1 is attached in a similar manner to the cable 22 associated with the patient monitor (PM1) to be used to display the information on the patient and optionally from which the patient ID 1 information was obtained. Further, depending upon the number of peripheral devices and patient monitors to be connected to the interface device 10, other PIDCAs 24 including the same or different patient ID information, e.g., patient ID 1 or patient ID 2, stored thereon can be connected between cables 16 and 22 extending between other patient peripheral devices, e.g., PD1B, PD2A and PD2B, and patient monitors, e.g., PM2.

In operation, when data is received by the interface device 10 from a peripheral device PD1A, PD1B, PD2A or PD2B, the PIDCA 24 connected to the cable 16 interconnecting that peripheral device PD1A, PD1B, PD2A or PD2B with the interface device 10 "codes" the incoming data in manner that allows the interface device 10 to direct that data from the input port 12 to the associated output port 14 and patient monitor PM1 or PM2 having the same code as provided by the separate PIDCA 24 connected to that specific output port 14. In one exemplary embodiment, the interface device 10 reads the Patient ID information from the PIDCAs 24 connected at input ports 12 and output ports 14. The software present within the interface device 10 then matches the ID from both input ports 12 and output ports 14 and then routes the data through the device 10 to the output port 14 where the ID from the PIDCA 24 at the input port 12 is matched. By using the PIDCAs 24 at both the input ports 12 and the output ports 14 of the multiport interface device 10, the multiport interface device 10 effectively routes the patient data to the correct patient monitor PM1 or PM2 for data aggregation. As a result, the potential for the mixing of patient data through the interface device 10 is significantly reduced. Further, the PIDCAs 24 provide a user with the flexibility to connect a peripheral device PD1A, PD1B, PD2A or PD2B to any input port 12 and a patient monitor PM1 or PM2 to any output ports 14, as the interface device 10 will route the data from the peripheral device PD1A, PD1B, PD2A or PD2B only to the similarly coded patient monitors PM1 or PM2. As a result, the PIDCAs 24 facilitate any number of configurations for the data flow through the interface device 10, without any modification to the internal components and/or circuitry of the interface device 10, and with the only limitation being the number of input ports 12 and output ports 14 physically present on the interface device 10. In addition, once a PIDCA 24 is done being used for a particular patient, the patient ID information stored in the memory chip 26 can be erased and the PIDCA 24 re-configured for use with a subsequent patient.

In another exemplary embodiment of the invention, the PIDCA 24 can additionally be utilized with patient monitors PM1, PM2 that have standard ports (not shown) for connecting the sensor cable 22 to the patient monitor PM1, PM2. For example, a patient monitor PM1, PM2 may have only USB ports with which to connect to the sensor cable 22 coming directly from the patient for data acquisition. In this case, since the standard port is not a dedicated port for a particular electrical parameter sensor, such as ECG, SpO2, temperature, etc., the use of a PIDCA 24 on the sensor cable 22 can significantly reduce the potential of a cable 22 being connected to the patient monitor PM1, PM2 from a different patient other than the patient associated with the PIDCA 24 and the specific patient monitor PM1, PM2.

In still another exemplary embodiment of the invention, it is contemplated that in addition to varying the number of peripheral devices and/or patient monitors, the number of peripheral devices associated with each patient monitor utilized in the system employing the interface device 10 can be varied. For, example, a system utilizing the interface device 10 can include a first patient monitor PM1 connected to peripheral devices PD1A-1C through the interface device 10, a second patient monitor PM2 connected to peripheral devices PD2A-2C through the interface device 10, and a third patient monitor PM3 connected to a single peripheral device PD3A through the interface device 10.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of directing data from one or more peripheral devices connected to a first patient to an associated patient monitor to minimize data mixing, the method comprising the steps of:
    a) determining the number of first peripheral devices operably connected to the first patient;
    b) configuring an interface device to direct data received from the number of first peripheral devices at a number of first input ports to a first output port;
    c) connecting the number of first peripheral devices to the number of first input ports; and
    d) connecting a first patient monitor to the first output port, wherein the step of configuring the interface device comprises the steps of:
        i) connecting one patient identification and communication adapter on which first patient ID information is stored between the number of first peripheral devices and the number of first input ports; and
        ii) connecting another patient identification and communication adapter on which first patient ID information is stored between the first patient monitor and the first output port.

2. The method of claim 1 further including the step of storing the first patient ID information on the patient identification and communication adapters prior to connecting the adapters to the number of first input ports and the first output port.

3. The method of claim 2 wherein the adapters include a near-field communication component, and wherein the step of storing the first patient ID information on the adapters comprises placing the adapters near the first patient monitor.

4. The method of claim 1 further comprising the steps of:
    a) determining a number of second peripheral devices operably connected to a second patient;
    b) configuring the interface device to direct data received from the number of second peripheral device at a number of second input ports to a second output port;
    c) connecting the number of second peripheral devices to the number of second input ports; and
    d) connecting a second patient monitor to the second output port.

5. The method of claim 4 wherein the step of configuring the interface device comprises the steps of:
    a) connecting first patient identification and communication adapters on which first patient ID information is stored between the number of first peripheral devices and the number of first input ports and between the first patient monitor and the first output port; and
    b) connecting second patient identification and communication adapters on which second patient ID information is stored between the number of second peripheral devices and the number of second input ports and between the second patient monitor and the second output port.

6. A system for directing patient data from peripheral devices connected to a first patient to a patient monitor, the system comprising:
   a) a multiport interface device having a number of input ports and a number of output ports
   b) a number of first peripheral devices connected between the first patient and a number of first input ports on the interface device; and
   c) a first patient monitor connected to a first output port of the interface device, wherein the interface device in configured to route incoming data from the number of first peripheral devices from the number of first input ports to the first output port; and
   d) a number of first patient identification and communication adapters on which first patient ID information is stored connected between the number of first peripheral devices and the number of first input ports and between the first patient monitor and the first output port.

7. The system of claim 6 further comprising:
   a) a number of second peripheral devices connected between a second patient and a number of second input ports on the interface device; and
   b) a second patient monitor connected to a second output port of the interface device, wherein the interface device in configured to route incoming data from the number of second peripheral devices from the number of second input ports to the second output port.

8. The system of claim 7 further comprising a number of second patient identification and communication adapters on which second patient ID information is stored connected between the number of second peripheral devices and the number of second input ports and between the second patient monitor and the second output port.

9. The system of claim 8 wherein the number of first patient identification and communication adapters each comprise:
   a) a near-field communication component; and
   b) a memory unit operably connected to the near-field communication component.

10. The system of claim 9 wherein the memory unit is re-writable.

11. The system of claim 9 wherein the number of first patient identification and communication adapters each comprise;
   a) a first connector operably engaged with one of the number of first peripheral devices or the first patient monitor; and
   b) a second connector operably engaged with one of the first input ports or the first output port of the interface device.

12. The system of claim 11 further comprising a number of first cables connected between the number of first peripheral devices and the number of first patient identification and communication adapters engaged with the number of first input ports.

13. The system of claim 11 further comprising a second cable connected between the first patient monitor and first patient identification and communication adapter engaged with the first output port.

* * * * *